(12) United States Patent
Morimoto et al.

(10) Patent No.: US 6,316,666 B1
(45) Date of Patent: Nov. 13, 2001

(54) METHOD FOR PRODUCING PURIFIED PHENYLENEDIOXYDIACETIC ACIDS

(75) Inventors: Junji Morimoto, Osaka; Takashi Kamikawa, Nara; Hiroshi Ueda, Osaka, all of (JP)

(73) Assignee: Sumitomo Chemical Company, Ltd., Osaka (JP)

( * ) Notice: Subject to any disclaimer, the term of this patent is extended or adjusted under 35 U.S.C. 154(b) by 0 days.

(21) Appl. No.: 09/495,951

(22) Filed: Feb. 2, 2000

(30) Foreign Application Priority Data

Feb. 2, 1999 (JP) .................................. 11-024926
Oct. 4, 1999 (JP) .................................. 11-282619

(51) Int. Cl.$^7$ .................................. C07C 59/48
(52) U.S. Cl. .................................. 562/471; 562/472
(58) Field of Search .................................. 562/471, 472

(56) References Cited

U.S. PATENT DOCUMENTS 3,951,599   4/1976   Davis et al. .

FOREIGN PATENT DOCUMENTS

| 1768900 | 1/1972 | (DE) . |
| 04091052 A | 3/1992 | (JP) . |
| 04173764 A | 6/1992 | (JP) . |

OTHER PUBLICATIONS

Abstract of JP 04 173764, Jun. 22, 1992.

*Primary Examiner*—Paul J. Killos
(74) *Attorney, Agent, or Firm*—Fitch, Even, Tabin & Flannery

(57) ABSTRACT

A method for producing phenylenedioxydiacetic acids of high purity at high yield from crude phenylenedioxydiacetic acids which mainly contains phenylenedioxydiacetic acids represented by the following general formula (I):

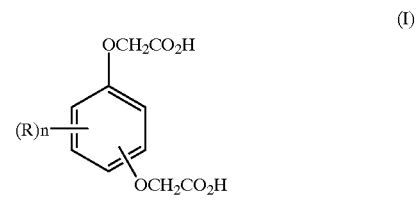

wherein, R represents a hologen, carboxyl group or hydrocarbon group having 1–4 carbon atoms, and n represents an integer from 0 to 3, wherein an alkaline aqueous solution of the crude phenylenedioxydiacetic acids is mixed with a mineral acid to precipitate the phenylenedioxydiacetic acids, wherein at least 10% by weight of the alkaline aqueous solution is mixed with a mineral acid at 0 to 50° C.; and, after completion of the mixing, the temperature of the mixture is kept at 80 to 110° C.

6 Claims, No Drawings

METHOD FOR PRODUCING PURIFIED PHENYLENEDIOXYDIACETIC ACIDS

The present invention relates to a method for producing purified phenylenedioxydiacetic acids.

Phenylonedioxydiacetic acids represented by the following general formula (I):

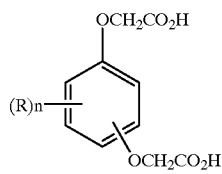

(I)

wherein, R represents a halogen, carboxyl group or hydrocarbon group having 1 to 4 carbon atoms, and n represents an integer from 0 to 3, are used as raw materials of polyesters, polyamides and the like and industrially useful compounds For producing purified phenylenedioxydiacetic acids, a method is known in which phenylenedioxydiacetic acids is precipitated from an alkaline aqueous solution of crude phenylenedioxydiacetic acids, which mainly contain phenylenedioxydiacetic acids, by the action of an acid. In an example of such methods, a mineral acid is used and the precipitation is conducted at a temperature of 80° C. or higher, followed by keeping the temperature of the system at 80° C. or higher (JP-A-4-173764).

However, in this method, the purity and the like of the resultant purified phenylenedioxydiacetic acids are not fully satisfactory, and improvements in these points hive been desired.

Under these circumstances, the present inventors have intensively studied the method for the precipitation of phenylenedioxydiacatic acids from an alkaline aqueous solution of crude phenylenedioxydiacetic acids by the action of an acid to obtain highly purified phenylenedioxydiacetic acids at high yield As a result, the present inventors have found that highly purified phenylenedioxydiacetic acids can be obtained at high yield by conducting the precipitation of phenylenedioxydiacetic acids from an alkaline aqueous solution of crude phenylenedioxydiacetic acids by mixing the solution with an acid at 0 to 50° C., followed by raising and keeping the temperature of the mixture at 80 to 110° C. The present inventor further found that at least 10% by weight or more of the phenylenedioxydiacetic acids needs to be precipitated at 0 to 50° C. in order to obtain intended highly purified products. The present invention was thus completed.

The present invention provides a method for producing purified phenylenedioxydiacetic acids in which an alkaline aqueous solution of crude phenylenedioxydiecetic acids which mainly contains phenylenedioxydiacetic acids represented by the following general formula (I):

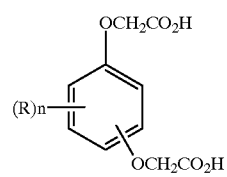

(I)

wherein, R represents a halogen, carboxyl group or hydrocarbon group having 1–4 carbon atoms, and n represents an integer from 0 to 3, is mixed with a mineral acid to precipitate the phenylenedioxydiacetic acids, wherein at least 10% by weight of the alkaline aqueous Solution is mixed with a mineral acid at 0 to 50° C.; and, after completion of the mixing, the temperature of the mixture is kept at 80 to 110° C.

The phenylenedioxydiacetic acids in the present invention is represented by the above-described general formula (I).

Examples of the substituent R in the f formula (I) include halogen atoms such as fluorine, chlorine and bromine, carboxyl group or salts thereof, and hydrocarbon groups having about 1 to 4 carbon atoms such as methyl, ethyl, t-butyl groups. in the formula (I), "n" is an integer of 0 to 3, and preferably 0.

Crude phenylenedioxydiacetic acids which are raw materials in the present invention mainly contain the above-described phenylenedioxydiacetic acids of formula (I).

The content of the phenylenedioxydiacetic acids of formula (I) in crude phenylenedioxydiacetic acids is preferably about 80% by weight or More, particularly preferably about 90% by weight or more in terms of solid components.

The alkaline aqueous solution of crude phenylenedioxydiacetic acids used in the present invention is an alkaline aqueous solution dissolving phenylenedioxydiacetic acids of the formula (I) ar well as impurities. It may further contain impurities as well as phenylenedioxydiacetic acids of the formula (I) which are not dissolved and are dispersed in the form of solid. That is, the alkaline aqueous solution of crude phenylenedioxydiacetic acids used in the present invention may be in the form of slurry.

The production method thereof is not particularly restricted and the following methods (1) and (2) can be exemplified.

(1) Dihydroxybenzenes represented by the following general formula (II)

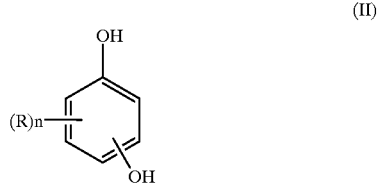

(II)

wherein, R and n are as defined above, are reacted with ethylene oxide in the presence of alkali, and the resulting phenylenedioxy diethanols are oxidized in an alkaline aqueous solution to obtain an alkaline aqueous solution of crude phenylenedioxydiacetic acids (JP-B62-28940, JP-A-3-500653 and JP-A-3-38544).

(2) Dihydroxybenzenes of the formula (II) and halogenated acetic acid are etherified in an alkaline aqueous solution to obtain an alkaline aqueous solution of crude phenylenedioxydiacetic acids (JP-A-4-173764).

Among the above, the method (2) is preferable since the content of phenylenedioxydiacetic acids in crude phenylenedioxydiacetic acids is higher.

Examples of the dihydroxybenzenes of the formula (II) include resorcinol and hydroquinone. Among them, resorcinol is preferred.

Examples of the halogenated acetic acid include monochloro acetic acid and monobromo acetic acid. Among them, monochloro acetic acid is preferred.

The amount of the halogenated acetic acid used in the method (2) is usually from about 2.0 to 4.0 mol, preferably from about 2.2 to 3.0 d mol per 1 mol of the dihydroxybenzenes.

Examples of the alkali used in the above-described method (2) include hydroxides, carbonates and the like of alkali metals such as sodium and potassium. Among them, sodium hydroxide and potassium hydroxide are preferable.

The amount of the alkali is usually from about 1.8 to 2.5 equivalent, preferably from about 1.9 to 2.1 equivalent per 1 mol of halogenated acetic acid.

The preferable concentration of an alkali in the aqueous solution varies depending on the kind of an alkali. In the case of sodium hydroxide, it is preferably from about 20 to 50% by weight.

The etherification reaction can be conducted, for example, by the following methods (1)–(3) as well as other methods.
(1) A halogenated acetic acid and an aqueous solution of alkali are poured together into an aqueous solution of dihydroxybenzenes.
(2) A halogenated acetic acid and an aqueous solution of alkali are poured together into a solution prepared by dissolving dihydroxybenzenes with a small amount of an aqueous solution of alkali, and then mixed.
(3) An alkaline aqueous solution containing dihydroxybenzenes dissolved and halogenated acetic acid are poured together in a reaction vessel and mixed.

The etherification reaction is conducted preferably at a pH of the reaction solution of about 7.5 to 12, more preferably of about 7.5 to 8.5. A pH of the reaction solution of less than 7.5 is not preferable since hydroxyphenyleneoxyacetic acid tend to increase. A pH over 12 is not preferable since then halogenated acetic acid tends to be hydrolyzed.

The etherification reaction is conducted at a temperature of usually from about 80 to 110° C., preferably from about 90 to 110° C.

The etherification reaction is preferably conducted until halogenated acetic acid in the reaction mass disappears. The reaction time is usually from about 1 to 10 hours.

In the present invention, an alkaline aqueous solution of crude phenylenedioxydiacetic acid; is mixed with a mineral acid to precipitate phenylenedioxydiacetic acids, and at least 10% by weight of the alkaline aqueous solution is mixed with a mineral acid at 0 to 50° C. Thereafter, the temperature of the mixture is raised and, after completion of the mixing, the temperature is kept at 80 to 110° C.

When leas than 10% by weight of an alkaline aqueous solution of crude phenylenedioxydiacetic acids is mixed with a mineral acid at 50° C. or lower, impurities in the resulting purified phenylenedioxydiacetic acids increase, and highly purified phenylenedioxydiacetic acids cannot be obtained. Although a temperature of leet than 0° C. is possible for mixing the alkaline aqueous solution with a mineral acid, such a temperature is economically undesirable since a cooling apparatus and the like are required.

Examples of the method for mixing the alkaline aqueous solution of crude phenylenedioxydiacetic acids with a mineral acid to precipitate phenylenedioxydiacetic acids include the following methods (1)–(6) as well as other methods.
(1) An alkaline aqueous solution of crude phenylenedioxydiacetic acids is added to a mineral acid at 0 to 50° C.
(2) An alkaline aqueous solution of crude phenylenedioxydiacetic acids and a mineral acid are poured together in a vessel and mixed at 0 to 50° C.
(3) A mineral acid is added to an alkaline aqueous solution of crude phenylenedioxydiacetic acids at 0 to 50° C.
(4) At least 10% by weight of an alkaline aqueous solution of crude phenylenedioxydiacetic acids is added to a mineral acid at 0 to 50° C., then, the remaining alkaline aqueous solution is added to a mineral acid at about 50 to 110° C. In this method, the temperature may be continuously raised from lower than 50° C. to higher than 50° C. as long as at least 10% by weight of the alkaline aqueous solution is added to a mineral acid before the temperature exceeds 50° C.
(5) At least 10% by weight of an alkaline aqueous solution of crude phenylenedioxydincetic acids and a mineral acid are poured together in a vessal and mixed at 0 to 50° C., then, the remaining alkaline aqueous solution and a mineral acid are poured together and mixed at about 50 to 110° C.
(6) A mineral acid is added to at least 10% by weight of an alkaline aqueous solution of crude phenylenedioxydiacetic acids at 0 to 50° C., them, the remaining alkaline aqueous solution and a mineral acid are mixed at about 50 to 110° C.

Among them, any of the methods (1), (2), (4) and (5) is preferable, and particularly, the method (1) or (4) is suitable, and the method (4) is more preferable.

Examples of the mineral acid used in the present invention include hydrochloric acid, sulfuric acid, nitric acid, phosphoric acid. Among them, sulfuric acid and hydrochloric acid are preferable, and particularly hydrochloric acid is preferable.

A mineral acid is preferably used in the form of an aqueous solution, and the concentration thereof is usually from about 5 to 20% by weight.

The amount of a mineral acid is usually from about 2.6 to 3.4 equivalents per 1 mol of phenylenedioxydiacetic acids of the formula (I).

After completion of mixing the alkaline aqueous solution of crude phonylenedioxydiacetic acids with a mineral acid to precipitate phenylenedioxydiacetic acids, the resulting mixture is Kept at 80 to 110° C., preferably at 85 to 95° C. The time for keeping temperature is usually from about 0. to 4 hours, preferably from about 0.5 to 2 hours When the keeping temperature is lower than 80° C., impurities in the resulting purified phenylenedioxydiacetic acids tend do increase, therefore noro preferable. On the other hand, when the keeping temperature is over 110° C., the mixture boils and a crystal adheres to the wall of a vessel, therefore not preferable.

After the keeping of tempeo-ature, the mixture is cooled to about 0 to 50° C., preferably about 10 to 40° C. Then, intended purified phenylenedioxydiacetic acids can be obtained by separating the resulting crystal by a measure such as filtration and the like, and if necessary, by washing with water and drying.

The resulting purified pbanylenedioxydiacetic acids can be further purified by recrystallization and the like, if necessary.

The following examples illustrate the present invention in more detail, but do not limit the scope of the present invention.

EXAMPLE 1

(Producing example of an alkaline aqueous solution of crude phenylenedioxydiacetic acids)

Into a flask was added 297.3 g (2.70 mol) of resorcinol and 225.0 g of water under nitrogen atmosphere. The mjxtuze was stirred to dissolve the resorcinol. Then, 48% sodium hydroxide water was added to control the pH of the solution to 7.8, then, the Solution was heated to 95° C. Thereto, an aqueous solution consisting of 663.4 g (7.02 mol) of monochloro acetic acid and 389.6 g of water was added at the same temperature over 5 hours, and the mixture was further stirred for 2 hours at the same tcmperature.

During the heating, addition of monochloro acetic acid and keeping temperature, 48% sodium hydroxide aqueous solution was added dropwise to control pH of the reaction system to 7.5 to 8.1. The total amount of the 48% sodium hydroxide aquveos solution used was 1110 g (4.93 equivalent). The resulting product was in the form of a slurry, and amount of the slurry was 2685 g. A part of this slurry was dissolved in a 50% acetonitrile aqueous solution, then, analyzed by an area percentage method using high performance liquid chromatography. The results are shown in Table 1.

(Producing example of purified phenylenedioxydiacetic acids)

Into a flask was charged 247.9 g (1.02 mol) of a 15% hydrochloric acid aqueous solution with stirring under nitrogen atmosphere, and the solution was cooled to 15° C. Therato, 297.0 g of the alkaline aqueous solution of crude phenylenedioxydiacetic acids (corresponding to 0.30 mol in terms of resorcinol) obtained above was gradually added The vessel used for producing the above alkaline aqueous solution of the crude phenylenedioxydiacetic acids was washed with 33 g of water and the washing water obtained was also added. One hour was required for addition of them. During this operation, the mixture in the flask was kept at 15±1° C.

Then, the resulting mixture was heated to 90° C. Thereafter, the mixture was kept at the same temperature for 1.0 hour, then, cooled to 30° C. The deposited crystal was filtered, and washed with 100 g of water. Then, vacuum drying was conducted at 60° C. to obtain 61.8 g of white purified phanylenedioxydiacetic acids. A part thereof was dissolved in a 50% acetonitrile aqueous solution, then, analyzed by an internal standard method using high performance liquid chromatography. The results are shown in Table 1.

EXAMPLE 2

Into a flask was charged 273.45 g (0.90 mol) of a 15% hydrochloric acid aqueous solution with stirring under nitrogen atmosphere, and the solution was cooled to 20° C. Thereto, 130.0 g of an alkaline aqueous solution of the crude phenylenedioxydiacetic acids obtained according to the same manner as in Examples 1 (corresponding to 0.13 mol in terms of resorcinol, and 43% of whole of the alkaline aqueous solution used in this example) was added. The reaction temperature in this operation was 50° C. Then, 172.54 g of an alkaline aqueous solution of the crude phanylenedioxydiacetic acids (corresponding to 0.17 mol in terms of resarcinol, and 57% of whole of the alkaline aqueous solution used in this example) was further added. The reaction temperature in this operation was 90° C. The vessel used for producing the above alkaline aqueous solution of the crude phenylenedioxydiacetic acids was washed with 33 g of water and the washing water obtained was also added One hour was required for addition of them.

Thereafter, the resulting mixture was kept at 90° C. for 1.0 hour, then, cooled to 30° C. The deposited crystal was filtered, and washed with 100 g of water Then, vacuum drying was conducted at 60° C. to obtain 63.0 g of a white crystal. The analysis results of the resulting crystal are shown in Table 1.

EXAMPLES 3 to 7 and Comparative Examples 1 to 3

According to Example 1 and 2 except that conditions shown in Table 1 were adopt, productions of purified phenylenedioxydiacetic acids were conducted. The results are shown in Table 1.

Regarding abbreviations used in Table 1, II-1 represents 3-phenylenedioxydiacetic acid, III-1 represents 1,3-hydroxyphenoxyacetic acid, and III-2 represents a mixture of 2-carboxymethyl-1,3-phenylenedioxydiacatic acid and 4-carboxymethyl-1,3-phenylenedioxydiacatic acid.

The term "Reaction Mass" in Table 1 indicates the crude phenylenedioxydiacetic acids used as the raw material.

The term "Product" in Table 1 indicates the purified product.

The term "intiation temperature" in Table 1 represents the temperature of a hydrochloric acid aqueous solution at the intiation of mixing of the hydrochloric acid aqueous solution with the alkaline aqueous solution of crude phenylenedioxydiacetic acids.

The term "termination temperature" in Table 1 represents the temperature of the mixture when mixing of the alkaline aqueous solution of crude phenylenedioxydiacetic acids with the hydrochloric acid aqueous solution was completed The term "addition amount" in Table 1 represents the weight ratio (%) of the alkaline aqueous solution mixed with the hydrochloric acid aqueous solution at 0 to 50° to the total weight of the alkaline aqueous solution of crude phenylenedioxydiacatic acids, and "time" in Table 1 represents the time required or mixig of a hydrochloric acid aqueous solution with all of an alkaline aqueous solution of crude phenylenedioxydiacetic acids. The term "keeping temperatures" in Table 1 represents the temperature of the mixture kept at the same temperature for 1 hour after mixing the hydrochloric acid aqueous solution with the alkaline aqueous solution of crude pbenylenedioxydiacetic acids was completed.

| | Example | | | | | | |
|---|---|---|---|---|---|---|---|
| | 1 | 2 | 3 | 4 | 5 | 6 | 7 |
| Reaction Mass | | | | | | | |
| II-1 | 92.09 | 93.13 | 92.27 | 92.09 | 92.94 | 93.13 | 91.87 |
| III-1 | 2.76 | 2.33 | 3.08 | 3.76 | 3.40 | 2.33 | 3.09 |
| III-2 | 4.00 | 4.55 | 4.60 | 4.00 | 3.62 | 4.55 | 5.04 |
| Initiation temperature (° C.) | 14 | 20 | 11 | 29 | 9 | 45 | 20 |
| Termination temperature (° C.) | 16 | 90 | 13 | 31 | 13 | 90 | 44 |
| Addition amount (%) | 100 | 43 | 100 | 100 | 100 | 11 | 100 |
| Time (min.) | 60 | 60 | 60 | 60 | 60 | 60 | 5 |
| Keeping temperature | 90 | 90 | 90 | 90 | 90 | 90 | 90 |
| Product | | | | | | | |
| II-1 | 99.46 | 98.70 | 98.70 | 98.33 | 99.90 | 99.02 | 99.48 |
| III-1 | 0.15 | 0.06 | 0.06 | 0.23 | 0.00 | 0.33 | 0.14 |
| III-2 | 0.21 | 0.11 | 0.11 | 0.44 | 0.02 | 0.52 | 0.13 |
| Yield (%) | 90.6 | 90.1 | 90.1 | 90.6 | 90.2 | 91.8 | 88.4 |

TABLE 1-2

| | Comparative example | | |
|---|---|---|---|
| | 1 | 2 | 3 |
| Reaction Mass | | | |
| II-1 | 92.09 | 92.27 | 92.62 |
| III-1 | 3.76 | 3.08 | 3.00 |
| III-2 | 4.00 | 4.60 | 4.62 |
| Initiation temperature (° C.) | 88 | 8 | 60 |
| Termination temperature (° C.) | 90 | 12 | 90 |
| Addition amount (%) | 0 | 100 | 0 |
| Time (min.) | 60 | 60 | 60 |
| Keeping temperature | 90 | 30 | 90 |
| Product | | | |
| II-1 | 92.55 | 86.49 | 97.28 |
| III-1 | 0.73 | 1.10 | 0.39 |
| III-2 | 1.66 | 1.48 | 0.99 |
| Yield (%) | 83.1 | 89.2 | 88.2 |

According to the present invention, highly purified phenylenedioxyacetic acids can be produced at high yield.

What is claimed is:

1. A method for producing purified phenylenedioxyacetic acids in which an alkaline aqueous solution of crude phenylenedioxyacetic acids which mainly contains phenylenedioxyacetic acids represented by the following general formula (I):

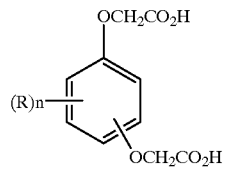

(I)

wherein, R represents a halogen, carboxyl group or hydrocarbon group having 1–4 carbon atoms, and n represents an integer from 0 to 3, is mixed with a mineral acid to precipitate the phenylenedioxydiacetic acids, wherein at least 10% by weight of the alkaline aqueous solution is mixed with a mineral acid at 0 to 50° C.; and, after completion of the mixing, the temperature of the mixture is kept at 80 to 110° C.

2. The method for producing purified phenylenedioxyacetic acids according to claim 1 wherein the alkaline aqueous solution of crude phenylenedioxyacetic acids is obtained by an etherification of a dihydroxybenzene represented by the following formula (II):

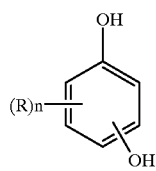

(II)

and a halogenated acetic acid in an alkaline aqueous solution.

3. The method for producing purified phanylenedioxyacetic acids according to claim 2 wherein the dihydroxybenzene is at least one selected from resorcinol and hydroquinone.

4. The method for producing purified phenylenedioxyacetic acids according to claim 2 wherein the halogenated acetic acid is monochloro acetic acid.

5. The method for producing purified phenylenedioxyacetic acids according to claim 1 wherein the mineral acid is at least one selected from sulfuric acid and hydrochloric acid.

6. The method for producing purified phenylenedioxyacetic acids according to claim 1 wherein, after completion of the mixing, the temperature of the mixture is kept at 80 to 110° C. for about 0.1 to 4 hours.

* * * * *